United States Patent
Parks et al.

(10) Patent No.: US 7,025,790 B2
(45) Date of Patent: Apr. 11, 2006

(54) ANKLE JOINT PROSTHESIS AND ITS METHOD OF IMPLANTATION

(75) Inventors: Brent G. Parks, West Friendship, MD (US); Christopher Chiodo, Norwood, MA (US); Lew C. Schon, Baltimore, MD (US); Steven Herbst, Baltimore, MD (US); Johnny Lau, Baltimore, MD (US)

(73) Assignee: Concepts In Medicine III, L.L.C., West Friendship, MD (US)

( * ) Notice: Subject to any disclaimer, the term of this patent is extended or adjusted under 35 U.S.C. 154(b) by 183 days.

(21) Appl. No.: 10/185,006

(22) Filed: Jun. 27, 2002

(65) Prior Publication Data
US 2004/0002768 A1 Jan. 1, 2004

(51) Int. Cl.
*A61F 2/42* (2006.01)
(52) U.S. Cl. .................... 623/21.18; 623/21.11
(58) Field of Classification Search ............ 623/18.11, 623/21.11, 21.18, 17.14, 17.15, 20.33
See application file for complete search history.

(56) References Cited

U.S. PATENT DOCUMENTS

| | | | |
|---|---|---|---|
| 3,839,742 A | 10/1974 | Link ................... | 3/1 |
| 3,872,519 A | 3/1975 | Giannestras et al. ........... | 3/1 |
| 3,886,599 A | 6/1975 | Schlein ............... | 3/1 |
| 3,889,300 A | 6/1975 | Smith ................ | 3/1.91 |
| 3,896,502 A | 7/1975 | Lennox ............ | 3/1.91 |
| 3,896,503 A | 7/1975 | Reykers et al. ........... | 3/1.91 |
| 3,975,778 A | 8/1976 | Newton ............ | 3/1.91 |
| 3,987,500 A | 10/1976 | Schlien ............ | 3/1.91 |
| 4,021,864 A | 5/1977 | Waugh ............. | 3/1.91 |
| 4,069,518 A | 1/1978 | Grouth et al. ........... | 3/1.91 |
| 4,156,944 A | 6/1979 | Schreiber et al. ........... | 3/1.91 |
| 4,232,404 A | 11/1980 | Samuelson et al. .......... | 3/1.91 |
| 4,470,158 A | 9/1984 | Pappas et al. ............. | 3/1.911 |
| 4,755,185 A | 7/1988 | Tarr ................ | 623/18 |
| 5,326,365 A | 7/1994 | Alvine ............... | 623/21 |
| 5,643,272 A | 7/1997 | Haines et al. ............. | 606/80 |
| 5,766,259 A | 6/1998 | Sammarco ............ | 623/21 |
| 6,183,519 B1 | 2/2001 | Bonnin et al. .......... | 623/21.18 |
| 6,205,411 B1 | 3/2001 | GiGioia et al. ........... | 703/11 |
| 6,217,619 B1 | 4/2001 | Keller ............... | 623/20.34 |

FOREIGN PATENT DOCUMENTS

| | | |
|---|---|---|
| DE | 19949890 | 10/1999 |
| EP | 1097680 | 11/1999 |
| EP | 1074230 | 8/2000 |
| FR | 2730157 | 2/1995 |
| FR | 2759900 | 2/1997 |

(Continued)

*Primary Examiner*—Brian E. Pellegrino
(74) *Attorney, Agent, or Firm*—Larry J. Guffey

(57) ABSTRACT

The ankle joint prosthesis adapted to involve the patient's distal tibia and talus has, according to the present invention, tibial, talar and mobile or semi-constrained bearing components that are laterally to medially implanted in the patient. The tibial component's top surface has convex curvature in its anterior to posterior plane and is configured so as to approximate and match with the curvature of a prepared portion of the distal tibia; its bottom surface being approximately flat. The talar component's top surface has saddle-shaped, convex curvature in its anterior to posterior plane, it's bottom surface has concave curvature and is configured so as to approximate and match with the curvature of a prepared portion of the talus. The mobile or semi-constrained bearing components have embodiments that comprise a wide variety of geometric shapes. A method for implanting such a prosthesis is also disclosed.

21 Claims, 22 Drawing Sheets

FOREIGN PATENT DOCUMENTS

| | | |
|---|---|---|
| FR | 2808994 | 5/2000 |
| WO | 0009046 | 8/1998 |
| WO | 0069373 | 5/1999 |
| WO | 0130264 | 10/1999 |
| WO | 0132109 | 11/1999 |
| WO | 0189427 | 5/2001 |

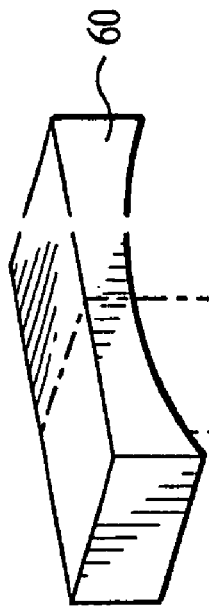 
FIG. 17B-1  FIG. 17B-2
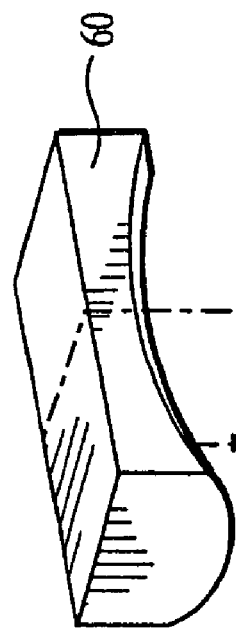 
FIG. 17A-1  FIG. 17A-2

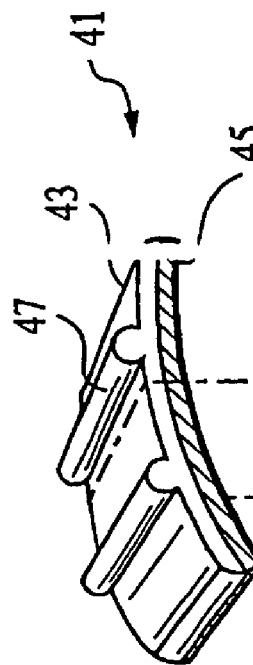
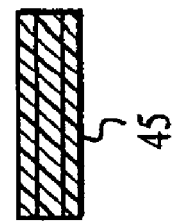
FIG. 18B-1    FIG. 18B-2
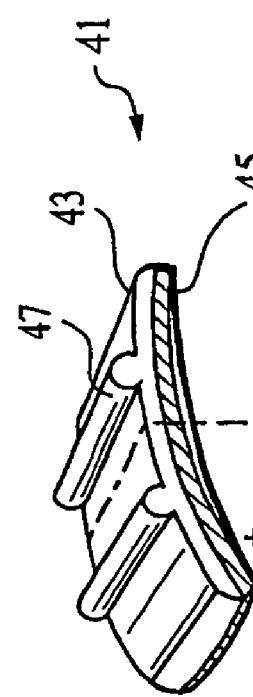
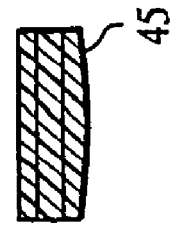
FIG. 18A-1    FIG. 18A-2

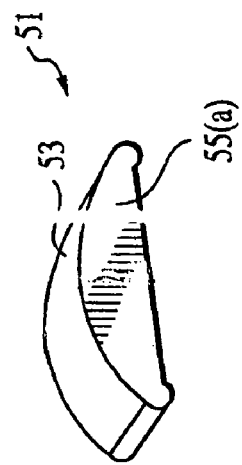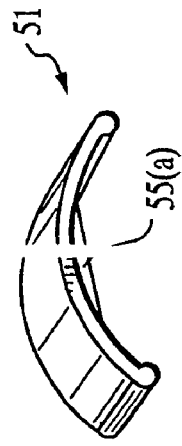
FIG. 20B-1    FIG. 20B-2    FIG. 20B-3
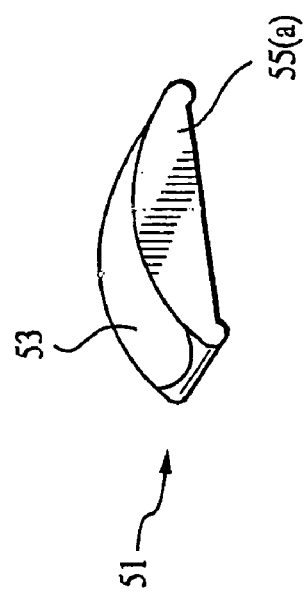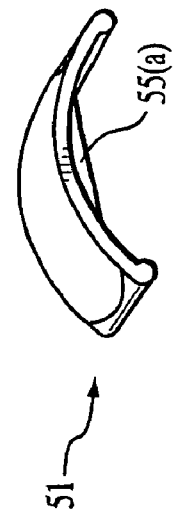
FIG. 20A-1    FIG. 20A-2    FIG. 20A-3

ANKLE JOINT PROSTHESIS AND ITS METHOD OF IMPLANTATION

BACKGROUND OF THE INVENTION

1. Field of the Invention

This invention relates to ankle prostheses and the surgical procedures for implanting such prostheses.

2. Description of Prior Art

For many years there has been considerable interest and activity with respect to ankle joint replacements, in which the degenerative articular surfaces are removed and replaced with an artificial joint called a prosthesis, as a viable approach to the treatment of diseased or injured ankle joints.

Fusion has long been an alternative to ankle arthroplasty. This approach has its drawbacks. For example, there is a loss of motion in the ankle joint which may cause difficulties with other associated parts of the foot and leg.

Many types of ankle joint prostheses have been developed over the past thirty years. After initial encouraging results, the reputation of ankle arthroplasty was somewhat damaged based on long-term, follow-up clinical studies which revealed the frequent failures of such implants due mainly to the inadequate restoration of the original mobility and the poor stability of the resulting ankle complex. Problems which many have speculated are due to our poor understanding of the relative contribution of the ligamentous structures and articular surfaces in providing passive and active stability for the ankle joint.

The ongoing problems with ankle arthrodesis have encouraged numerous ankle arthroplasty designs. The early designs all feature two-component prostheses having talar and tibial components for respective attachment to the talar and tibia bones of the ankle. For example, see U.S. Pat. Nos. 4,156,944, 4,069,518, 4,021,864, 3,987,500, 3,975,778, 3,896,503, 3,896,502, 3,889,300, 3,86,599, 3,872,519, and 3,839,742.

Despite the multitude of these designs, none of them yielded clinical results comparable to those achieved with total hip and knee replacement surgeries. Aseptic loosening of the tibial and/or talar components is reportedly the most frequent cause of failure, but complications also included deep infections, dehiscence of the surgical wound, lateral and/or medial subluxation of the floating meniscus and lateral talofibular joint impingement.

The most recent prosthesis design feature three components and include a floating, intermediate element that has been introduced to allow full congruence at the articular surfaces in all joint positions in order to minimize wear of the components while coping with the multi-axial nature of the axial rotation of the ankle. These designs all feature a planar and a curved surface for the intermediate element in order to allow a controlled freedom of motion relative to the tibial component, allowing controlled anterior-posterior as well as medial-lateral motion in such a way as to reduce wear of the surfaces and the stress at the interface between the bone and the tibial component of the prosthesis. For example, see U.S. Pat. Nos. 4,470,158, 4,755,259 and 5,766,259. These three component designs are also reported to have exhibited problems with aseptic loosening of the tibial and/or talar components, migration of the prosthesis and inadequate motion in the replaced joint.

A common characteristic among these previous total ankle prostheses is that they are inserted through incisions made with an anterior approach to the ankle joint. This approach requires making large incisions at the ankle and moving the tendons and other soft tissue aside; thus violating important anterior soft-tissue structures and, more importantly, neurovascular structures that provide blood flow to the talus.

Despite the extensive development of ankle joint prostheses, they often continue to exhibit less than desirable performance. Thus, there exists a continuing need for the development of new and improved types of such devices. There is also a need for a less invasive surgical method to install such a prostheses so as to yield improved healing and a decrease in the failure rate of such devices.

3. Objects and Advantages

There has been summarized above, rather broadly, the prior art that is related to the present invention in order that the context of the present invention may be better understood and appreciated. In this regard, it is instructive to also consider the objects and advantages of the present invention.

It is an object of the present invention to provide an improved ankle joint prosthesis that decreases the failure rate currently being experienced by such devices.

It is another object of the present invention to provide a less invasive surgical method for inserting an ankle joint prosthesis so as to yield improved healing and a decrease in the failure rate of such devices.

It is yet another object of the present invention to provide a surgical method that utilizes a lateral approach, as opposed to the standard anterior approach, for inserting an ankle joint prosthesis.

It is a further object of the present invention to provide a surgical method for implanting ankle joint prostheses that utilizes a lateral approach, as opposed to the standard anterior approach, so as to preserve the blood supply to the talus, thereby avoiding the avascular pathologies known to be caused by damaging the blood supply to the talus.

It is an object of the present invention to prepare the ankle joint for the insertion of an ankle joint prosthesis using a crescentic shaped saw, which allows for minimum bone resection that follows the natural contours of the joint and preserves the strongest portion of the distal tibia and talus for implantation of an ankle prosthesis.

It is an object of the present invention to provide an ankle joint prosthesis having components that have crescentic shaped surfaces for attachment with the adjoining tibia and talus bones so as to provide more surface area for bony ingrowth or cement fixation than that provided by standard prostheses which use flat surfaces.

It is an object of the present invention to present an ankle joint prosthesis with different levels of constraint, ranging from unconstrained to semi-constrained. This provides options for dealing with different clinical situations. Ultimately, the goal will be to use an ankle joint prosthesis, which minimizes wear and enhances the longevity of the implant.

It is a still further object of the present invention to provide a device and method that will advance the effectiveness of ankle joint replacements in orthopedic medicine.

These and other objects and advantages of the present invention will become readily apparent as the invention is better understood by reference to the accompanying summary, drawings and the detailed description that follows.

SUMMARY OF THE INVENTION

Recognizing the need for the development of improved ankle joint prostheses and their methods for insertion, the present invention is generally directed to satisfying the needs set forth above and overcoming the disadvantages identified with prior art devices and methods.

In accordance with the present invention, the foregoing need can be satisfied by providing an ankle joint prosthesis adapted to involve the patient's distal tibia and talus. This prosthesis may have many embodiments.

In a preferred, mobile bearing embodiment, the prosthesis comprises tibial, talar and mobile bearing components that are laterally to medially implanted in the patient. The tibial component's superior (top) surface has convex curvature in the anterior to posterior direction and is configured so as to approximate and match with the curvature of a prepared portion of the distal tibia; its inferior (bottom) surface is approximately flat. The talar component's top surface has one of two forms of curvature. It has only convex curvature in the anterior to posterior direction or it has this curvature plus concave curvature in the lateral to medial direction. Its bottom surface has concave curvature in the anterior to posterior direction and is configured so as to approximate and match with the curvature of a prepared portion of the talus. The mobile bearing component's top surface is approximately flat, and its bottom surface has curvature that is complementary to the curvature of the talar component's top surface.

In a preferred, semi-constrained bearing embodiment, the prosthesis comprises tibial, semi-constrained bearing and talar components that are laterally to medially implanted in the patient. In this instance, the tibial component's top surface has convex curvature in the anterior to posterior direction and is configured so as to approximate and match with the curvature of a prepared portion of the distal tibia; its bottom surface has concave curvature in the anterior to posterior direction. The talar component's top surface has curvature that is configured to be complimentary with the curvature of the semi-constrained bearing component's bottom surface so as to allow maximal surface contact. Its bottom surface has concave curvature in the anterior to posterior direction and has protrusions at its anterior and posterior ends that protrude downward. The semi-constrained bearing component has a top surface with curvature that is complimentary with the curvature found in the bottom surface of the tibial component so as to lock these surfaces together in various levels of constraint. Polyethylene or another suitable bearing material is used for constructing the semi-constrained bearing component.

According to a third embodiment of the present invention, a method is provided for laterally to medially implanting an ankle joint prosthesis so as to replace the diseased bone associated with the articulating surfaces between a patient's distal tibia and talus. The method comprises the steps of (a) making an incision on the lateral side of the foot and ankle opposite the joint, (b) cutting the patient's fibula at a point above the joint and reflecting the inferior portion of the fibula downward so as to gain access to the ankle joint, (c) distracting the ankle joint so as to improve access to the joint, (d) making a lateral to medial, crescentic cut on the end portion of the distal tibia so as to prepare a portion of the tibia by removing the diseased bone and configuring the prepared portion so that it matches the anterior to posterior, cross-sectional profile of a to-be-inserted tibial component, (e) making a lateral to medial, crescentic cut on the dome portion of the talus so as to prepare a portion of the talus by removing the diseased bone and configuring the prepared portion so that it matches the anterior to posterior plane profile of a to-be-inserted talar component, (f) preparing one or more lateral to medial recesses in the cut surfaces of the tibial and talus, (g) laterally to medially inserting the tibial component in the prepared portion of the tibia, (h) laterally to medially inserting the talar component in the prepared portion of the talus, (i) if a mobile bearing prosthesis is being used, laterally to medially inserting a mobile bearing component between the tibial and talar components, or, if a semi constrained bearing prosthesis is being used, laterally to medially inserting a semi constrained bearing component between the tibial and talar components, (j) removing distraction from the ankle joint, (k) replacing the inferior portion of the fibula back into position relative to the upper portion of the fibula and securing the portions in position, and (l) closing the opening incision.

Thus, there has been summarized above, rather broadly, the present invention in order that the detailed description that follows may be better understood and appreciated. There are, of course, additional features of the invention that will be described hereinafter and which will form the subject matter of any eventual claims to this invention.

BRIEF DESCRIPTION OF THE DRAWINGS

FIGS. 17A-1 and 17A-2 show perspective and cross-sectional views of a preferred embodiment of the mobile bearing component of the present invention in which the component's bottom surface is saddle shaped and has concave curvature in the anterior to posterior direction and convex curvature in the lateral to posterior direction.

FIGS. 17B-1 and 17B-2 show perspective and cross-sectional views of a preferred embodiment of the mobile bearing component of the present invention in which the component's bottom surface has concave curvature only in the anterior to posterior direction.

FIGS. 18A-1 and 18-2 show perspective and a cross-sectional views of a preferred embodiment of the tibial component in a semi-constrained version of the present invention in which the component's bottom surface is saddle shaped and has concave curvature in the anterior to posterior direction and convex curvature in the lateral to posterior direction.

FIGS. 18B-1 and 18B-2 show perspective and a cross-sectional views of a preferred embodiment of the tibial component in a semi-constrained version of the present invention in which the component's bottom surface has concave curvature only in the anterior to posterior direction.

FIGS. 20A-1 to 20A-3 show respective lateral, anterior and medial views of a preferred embodiment of a talar component whose top surface has saddle shaped curvature.

FIGS. 20B-1 to 20B-3 show respective lateral, anterior and medial views of a preferred embodiment of a talar components whose top surface has only convex curvature in the anterior to posterior direction.

DETAILED DESCRIPTION OF THE PREFERRED EMBODIMENT

Figure 1:
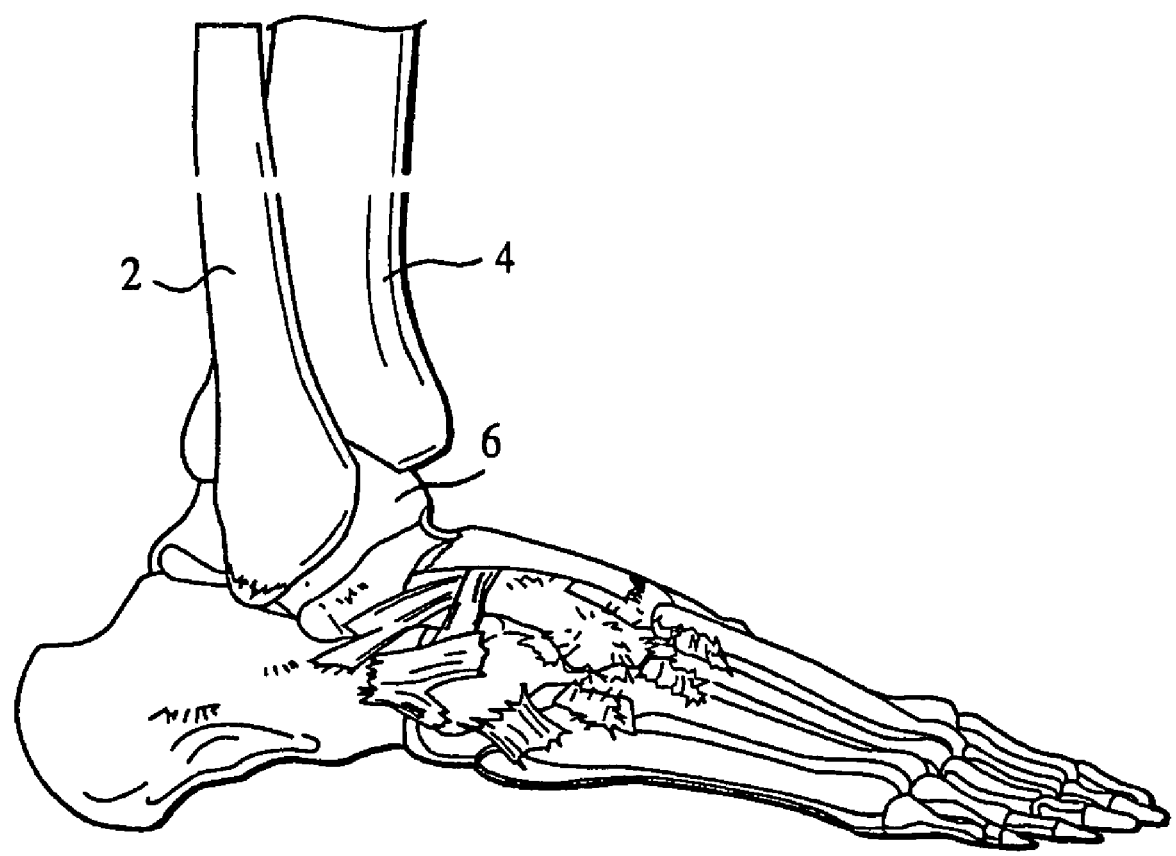
FIG. 1 is a lateral elevational view of a right, human foot.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Referring now to the drawings wherein are shown preferred embodiments and wherein like reference numerals designate like elements throughout, there is shown in FIG. 1 a lateral, elevational view of a right, human foot that illustrates most of the foot bones and the lower ends of the lower leg bones. The present invention involves three of these bones: the fibula 2, the tibia 4 and the talus 6.

Figure 2:
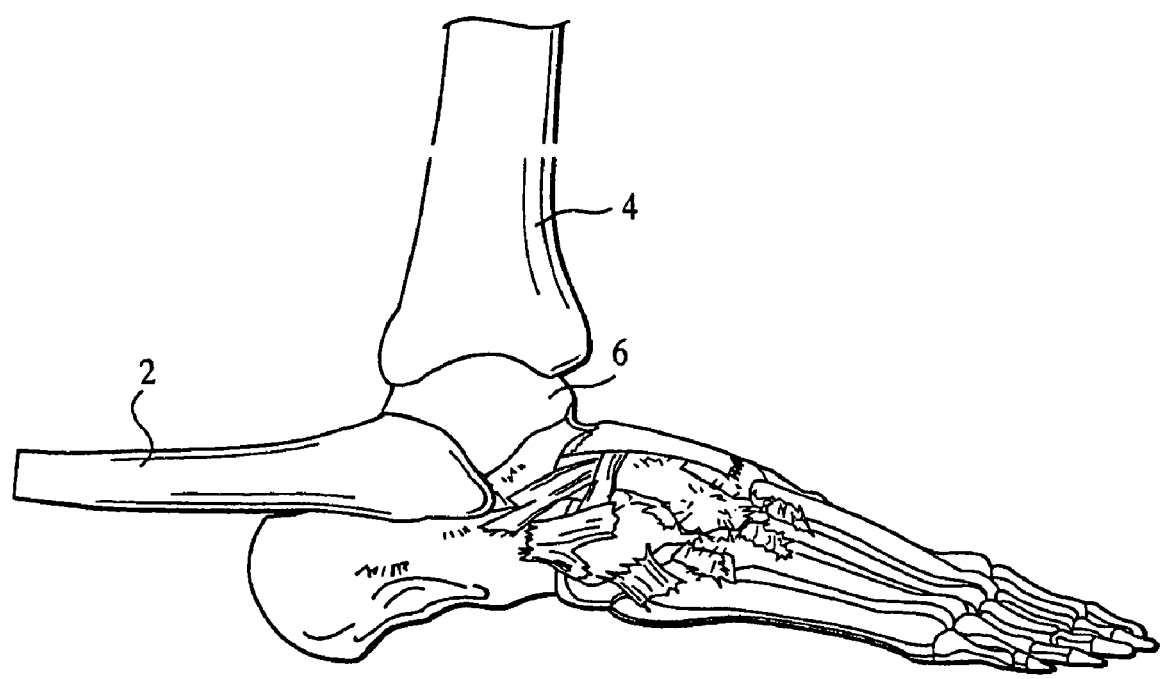
FIG. 2 is a similar view of the foot in FIG. 1 and showing the fibula having been cut and moved down to gain lateral access to the ankle joint.
Figure 3:
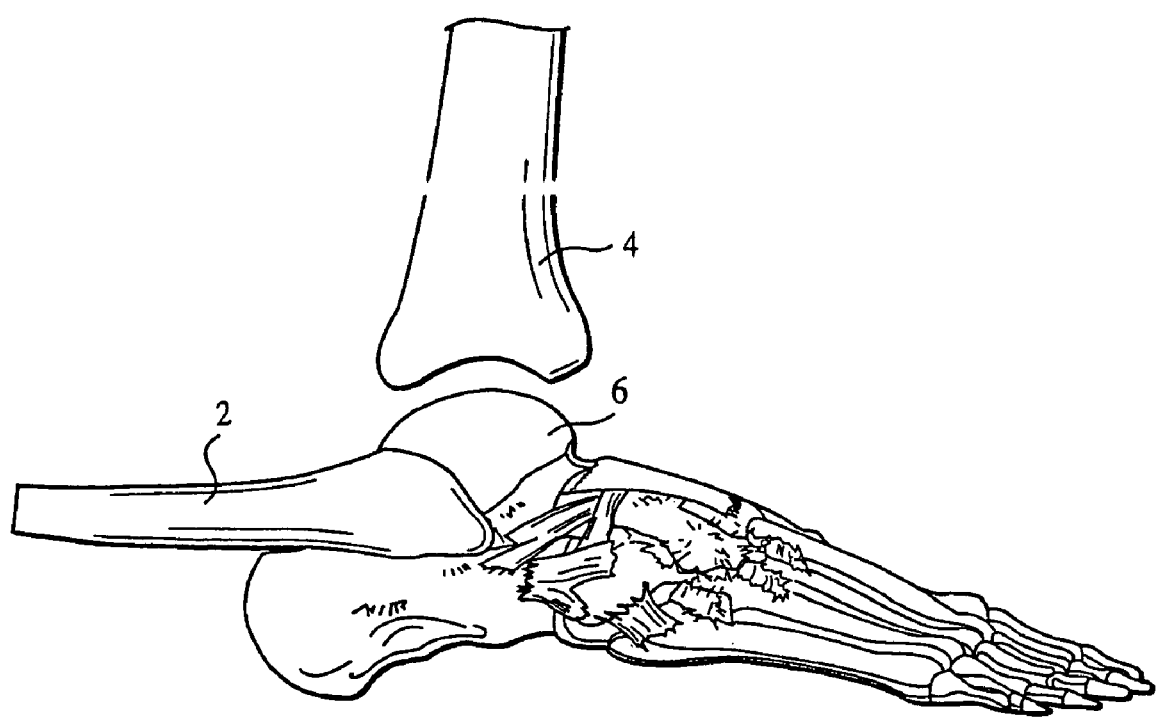
FIG. 3 is a similar view of the foot in FIG. 1 and showing the ankle joint distracted so as to provide better lateral access to the ankle joint.

To gain lateral access to the ankle joint, the fibula 2 is cut at a point above its lower end and this lower end is moved to the side. See FIG. 2. The distal end of the fibula is reflected down hinged on the posterior talofibular and calcaneofibular ligaments. The syndesmosis, anterior talofibular and part of the calcaneofibular ligaments are released from the fibula. The ankle joint is distracted manually or by using an unilateral external fixator applied to the medial aspect. This gives better access to the distal tibia and talar dome surfaces that are to be cut. See FIG. 3.

Figure 4:
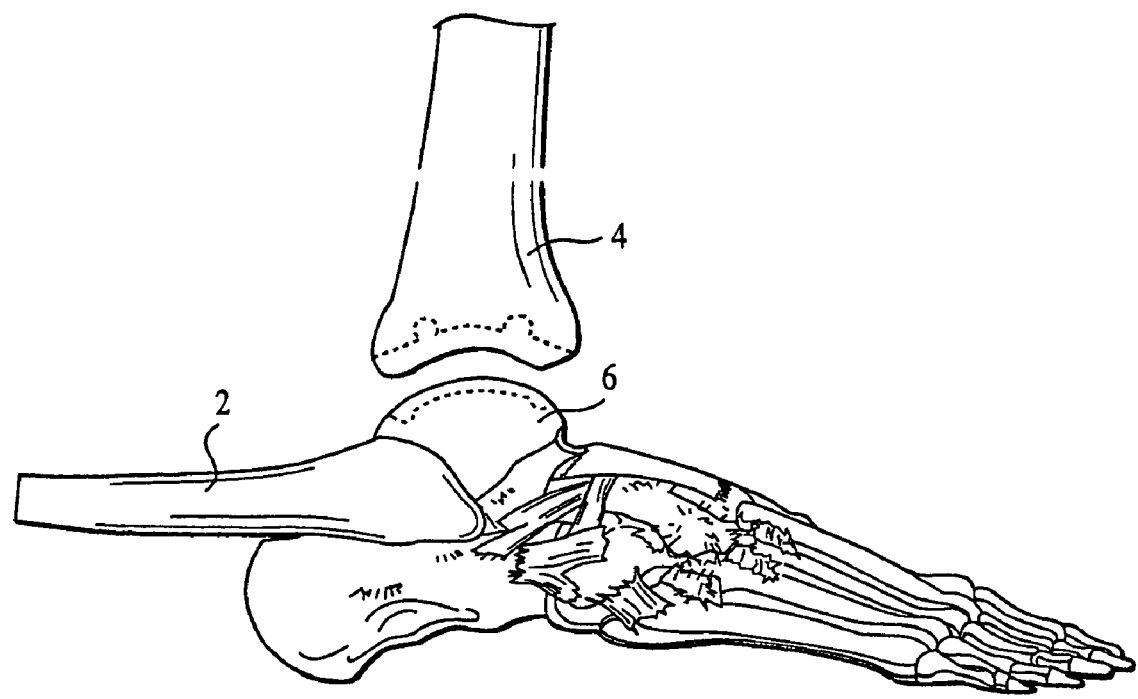
FIG. 4 is a similar view of the foot in FIG. 1 and showing by dashed lines the shape of the cuts to be made in the surfaces of the distal tibia and talar dome.

FIG. 4 shows by dashed lines the approximate shape of the cuts that are to be made in the surfaces of the distal tibia and talar dome. The geometry of these cuts is crescentic since it closely follows the natural anatomic contour of the joint and its subchondral bone of the distal tibia and talus.

The crescentic cut yields more bony surface area for cement fixation or bony ingrowth. The lateral approach, which exposes the ankle joint surface, allows a reproducible method for minimizing bone loss while performing accurate crescentic cuts. The precision of crescentic cuts that follows the natural anatomic contour of the joint and its subchondral bone, allows for the preservation of the strongest portions of the distal tibia and talus. This is the best bone in which to implant an ankle arthroplasty and may improve survival of ankle joints. Furthermore the tenuous blood supply of the talus, which more typically is compromised with an anterior approach, is left intact with the lateral approach. The distal tibia blood supply is similarly preserved through a lateral approach. The lateral approach minimizes soft tissue compromise as opposed to the anterior approach.

Three basic cuts are required to remove the bone necessary to allow for implantation of the prosthesis. One crescentic cut at the talar dome to remove diseased/damaged cartilage and bone. A second cut in the anterior-posterior direction to free the lateral aspect of the medial wall. A third and final, crescentic cut on the distal end of the tibia in a lateral-medial direction. This third cut will intersect with the second cut on the medial wall of the distal tibia to free the distal segment of tibial bone.

Figure 5:
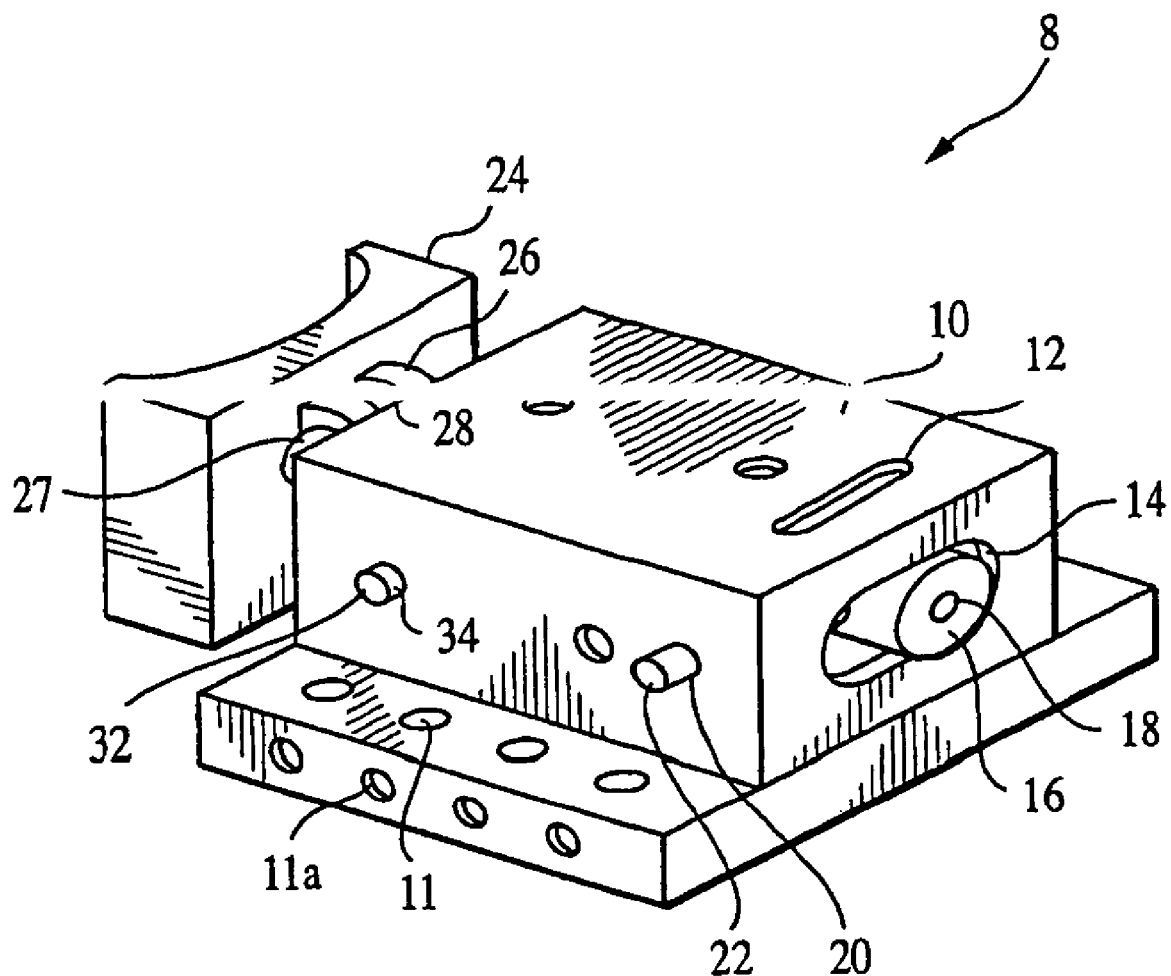
FIG. 5 is a perspective, side view of a special cutting guide that is used to make the cuts in the surfaces of the distal tibia and talar dome.

These cuts are made with the aid of a special cutting guide 8 that is shown in FIG. 5. It consists of a base 10 which has a plurality of anchoring holes 11 through which one or more anchoring or mounting pins may be extended for anchoring with the patient's tibia. Set screw holes 11a in the side of the base allow set screws to be used to fix the position of the base relative to the pins that extend from the patient's tibia. The slotted hole 12 on the top of the base is placed over a mounting pin in the patient's tibia to provide a preferred initial means for securing the base to the patient's tibia.

At the back of the base, a slotted cavity 14 has been provided to allow for the placement of a locking cylinder 16 in the base 10. The locking cylinder fits within this cavity with its distal end generally extending toward the front of the base. This cylinder has a hole that extends from its exterior surface and intersects a threaded bore 18 that extends along the axis of the cylinder from the cylinder's proximate end which is exposed in the entrance to base's rear cavity. The slotted hole 12 on the top of the base extends into the cavity 14 created in the rear of the base and then through the bottom portion of the base, so that this slotted hole 12 extends all the way through the base .

Figure 6:
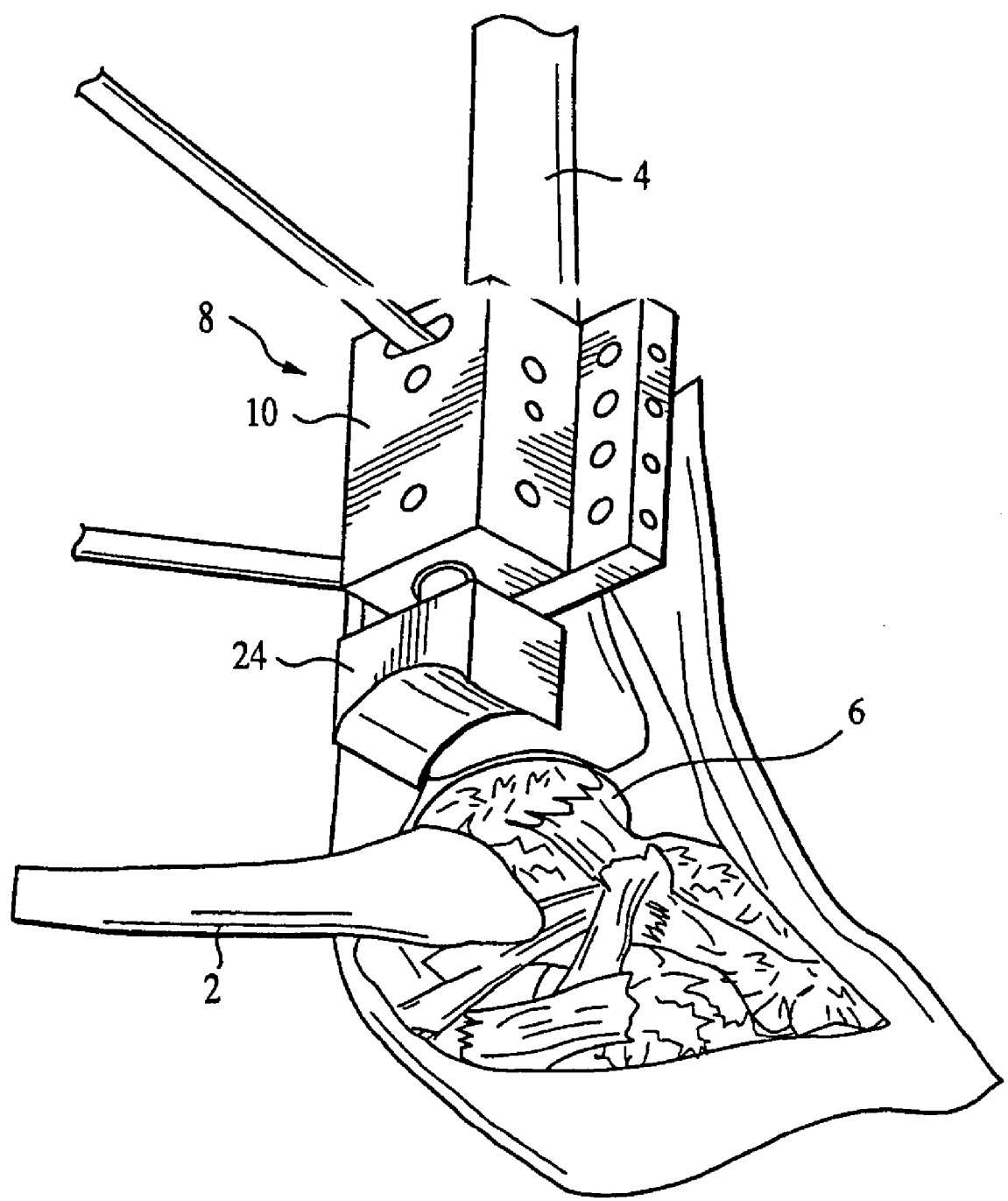
FIG. 6 shows the special cutting guide of FIG. 5 in use for surgically removing a portion of the adjoining tissue between the top of the talus and the bottom of the tibia.

In use, see FIG. 6, the cylinder 16 is placed such that the pin from the patient's tibia also extends through the hole in the cylinder's exterior surface. The cylinder is secured to the pin by a set screw that fits within the cylinder's threaded, axial bore 18 and can be turned by accessing the set screw's free end which is exposed at the cylinder's proximate end. From each side of the base extend additional threaded bores 20 that project into the sides of the bases' rear cavity 14. These bores contain set screws 22 that can be tighten to lock the cylinder 16 in place relative to the rest of the base 10. The advantage of this configuration is that it provides the surgeon with a means to adjust the location of the base 10 relative to the locking cylinder 16 which is locked to the pin in the patient's tibia. Thus, the locking cylinder 16 can be moved to either side or rotated about a vertical axis defined by the axis of the pin that extends from the patient's tibia.

The centerlines of the anchoring holes 11 which are located in the base's top surface and towards its outer edges are slanted towards and at an angle with respect to the base's longitudinal centerline. This angle is provided so as to allow the pins that pass through these holes to approximately contact the tibia perpendicularly to its surface. This allows these pins to be directed towards the tibia's centerline so as to provide the pins with the most secure attachment to the bone.

To the front of this base 10 is attached a shelf 24; the front surface of which is shaped so as to have the curvature that is desired to be used in the cut that is made in the surfaces of the distal tibia and talar dome . The surgeon places his curved blade against the shelf's front surface to guide his cuffing during the surgical procedure.

The shelf 24 is mounted so that it can be pivoted up and down about a pivot joint 26 which is mounted on the back of the shelf. A set screw 27 allows the angular rotation of the pivot joint 26 to be fixed. Additionally, the nature of this connection is such that the shelf can easily be detached from the shaft. This allows for the opportunity to interchange the shelf that is attached to a shaft so that a shelf can be selected from a group of the various surface curvatures, with appropriate protrusions, that will be needed during the surgery.

From the shelf's pivot joint, there extends a shaft 28 which can slip into and out of a cavity that exists in the front of the base. On the side of the base there exist two additional bores 32 in which are placed set screws 34 that can be screwed inward so as to contact the exterior surface of the shaft 28 that extends into the base's front cavity. Thus, the distance between the back of the shelf and the front of the base can be set by the use of these set screws to lock the shaft relative to the base. With this configuration, the shelf's position is adjustable in three directions: forward and backward as the shaft moves in and out of the base, rotationally about the axis of the shaft which can rotate within the base's front cavity, and rotationally (i.e., up and down, assuming that the ends of the shelf are extending horizontally) about the hinge joint that connects the front of the shaft and the back of the shelf.

After the necessary incisions have been made to expose the ankle joint and the fibula has been cut and peeled back to allow full access to the joint, the cutting guide 8 is placed on the tibia at the location where its shelf 24 can best be utilized in making the necessary cuts on the talus and the tibia. In order to assist in achieving the ideal alignment of the bone cuts and prosthetic components, a modification of the cutting guide 8 may be introduced to facilitate restoration of anatomic, physiologic, and biomechanical alignment.

Pre-operative x-rays of the normal contra-lateral ankle are obtained. The normal ankle x-rays are compared to the diseased ankle. The side of the diseased ankle joint, which is the least damaged, is identified in both the anterior-to-posterior and lateral ankle x-rays. These points in the x-rays help to restore the normal architecture and ankle joint level.

Figure 7:
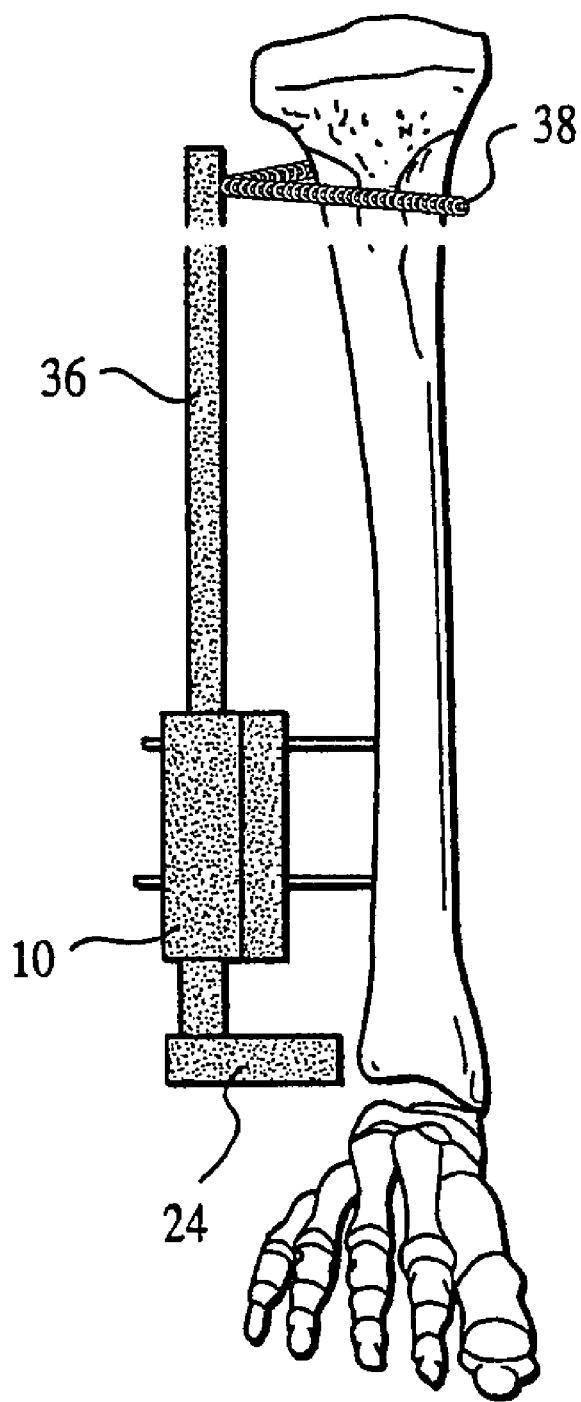
FIG. 7 shows an anterior view of the alignment rod being used with the special cutting guide.

An alignment rod 36 is attached to the cutting guide 8 and extends proximally to the knee. See FIG. 7. The alignment rod 36 is held in this position and stabilized to the knee proximally with a coiled spring 38, and to the ankle distally with the transfixion pins.

Figure 8:
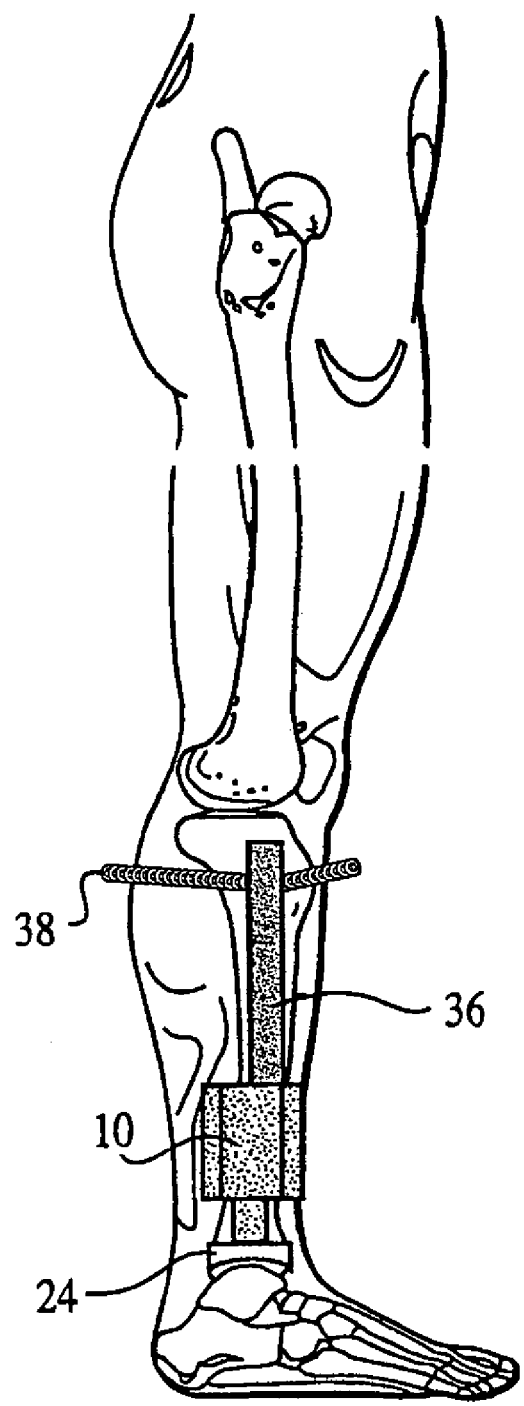
FIG. 8 shows an lateral view of the alignment rod being used with the special cutting guide.

A lateral x-ray of the tibia is obtained and the alignment rod 36 is positioned to align centrally down the intramedually canal of the tibia from the knee, proximally, and the ankle, distally. See FIG. 8.

The alignment rod 36 is used as a reference for the alignment of the ankle joint line in the anterior to posterior plane, which is perpendicular to the alignment rod 36.

To establish the alignment of the ankle joint in the lateral and medial plane, an anterior-to-posterior ankle x-ray is taken. A narrow wire is passed in the cutting guide 8 from lateral to medial on the anterior aspect of the ankle joint. The height of the crescentic cut is adjusted until the narrow wire is located just proximal to the portion of the ankle joint which has the least amount of damage as determined on the x-rays of the normal ankle joint.

The orientation above the tibia of the base's top, slotted hole 12 serves to define the site for the drilling of a hole for the insertion of a primary mounting pin in the tibia. After this pin is inserted, its extended end is fed through the base's top, slotted hole 12 and through the locking cylinder's hole. The cylinder's set screws are then tightened to be to lock the cutting guide 8 in place.

The surgeon next chooses one or more of the side holes 11 for use in anchoring to secondary mounting pins which are passed through these holes 11 and into the tibia. For each of these pins, a pilot hole is initially drilled in the bone and a secondary mounting pin is inserted through the hole 11. A set screw 11a is again used to lock the cutting guide to each of these secondary mounting pin. Once the cutting guide is securely locked to the mounting pins, the shelf 24 of the apparatus can be further adjusted and aligned to ensure that it is properly located to most effectively assist the surgeon in making the necessary cuts.

The cutting guide 8 may be made of any appropriate material, such as stainless steel, or the like, which is suitable for use in a surgical environment and is capable of being sterilized.

Figure 9:
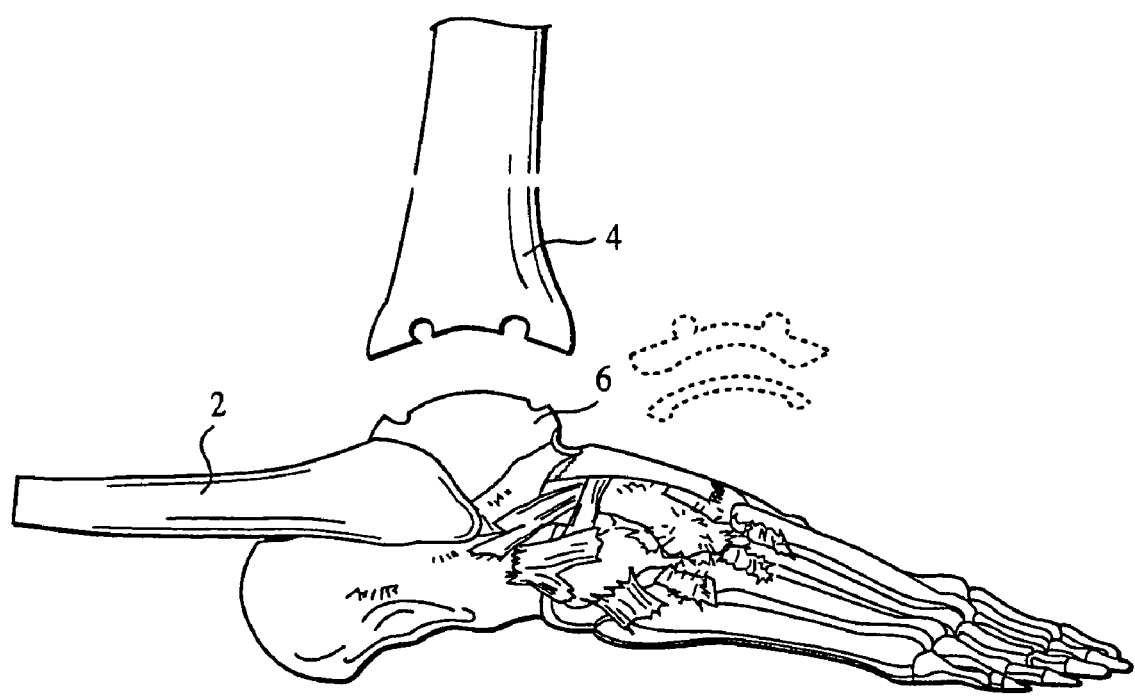
FIG. 9 is a similar view of the foot in FIG. 1 and showing the distal tibia and talar dome after the necessary portions have been removed.
Figure 10A:
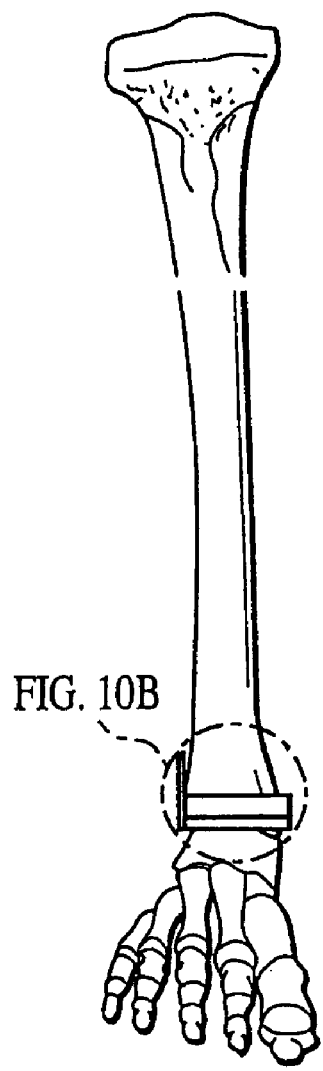
FIG. 10A is an anterior, in-situ view of a talar, lateral surface cutting guide that is used to cut the lateral surface of the talus dome.
Figure 10B:
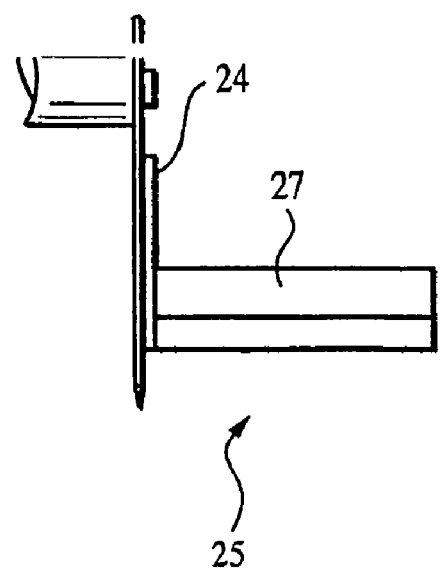
FIG. 10B is a close-up view of the cutting guide shown in FIG. 10A.
Figures 11A, 11B:
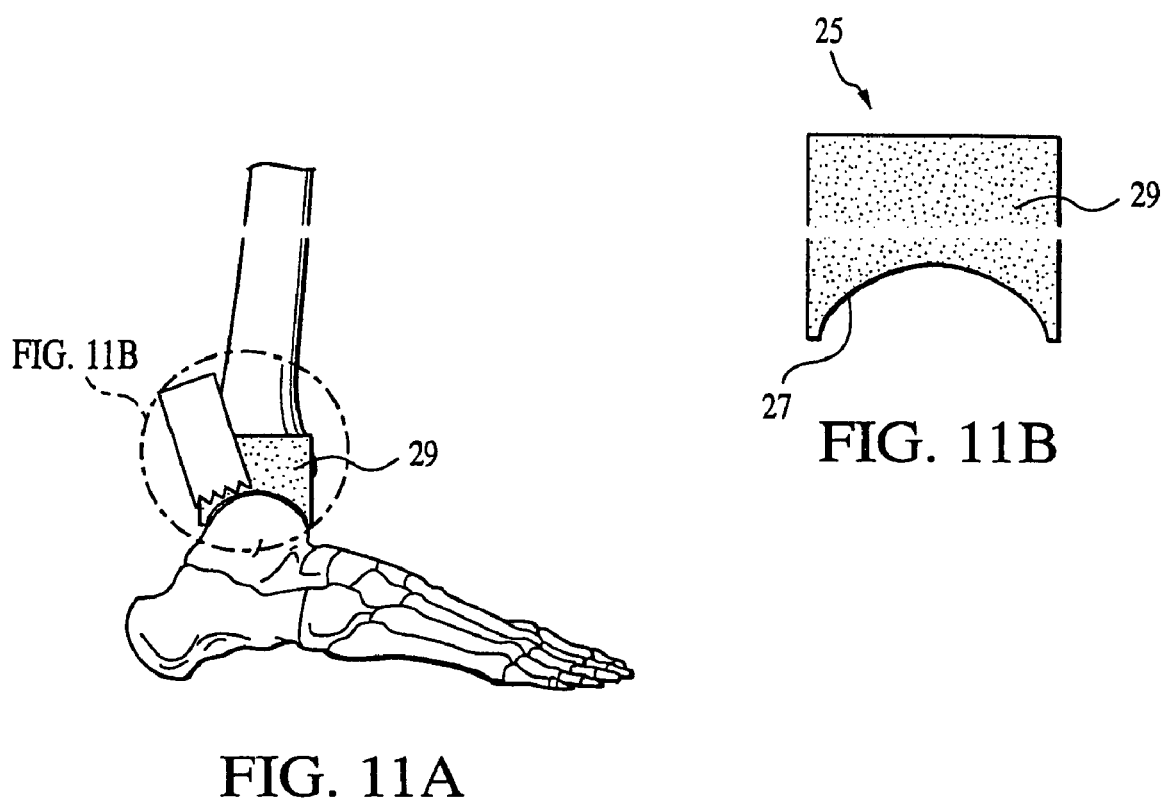
FIG. 11A is a lateral, in-situ view of the cutting guide shown in FIG. 10A.
FIG. 11B is a close-up view of the cutting guide shown in FIG. 11A.

FIG. 9 shows the distal tibia and talar dome after the necessary portions have been removed. These portions are removed with the assistance of a talar, lateral surface cutting guide 25. The talar lateral surface cutting guide is used to cut the lateral surface of the talus. This provides a flat mating surface for the inside of the talar component. This surface cutting guide 25 is composed of a curved piece 27 which acts as a cutting guide shelf and is adjoined to a vertical element 29 extending superior to inferior on the lateral edge of the cutting shelf. See FIGS. 10A and 10B. The curved piece 27 is narrow so that it can be positioned between the distracted tibia and talus. The curved piece 27 is then held flush against the superior aspect of the talus and pushed medially such that the lateral edge of the talus protrudes lateral to the vertical element of the cutting shelf. An oscillating saw is then used to cut the lateral aspect of the talus. This talar lateral surface cut is not required when using an approximately flat cut on the talus. See FIGS. 11A and 11B. These prepared surfaces correspond to the bone-metal interface surfaces the prosthetic components.

Figure 12B:
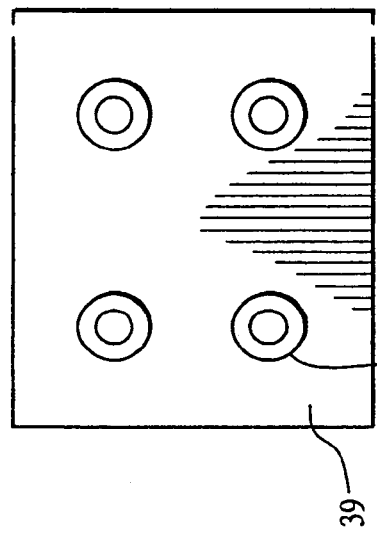
FIG. 12B is a lateral view of the recess cutting guide shown in FIG. 12A.
Figure 12C:
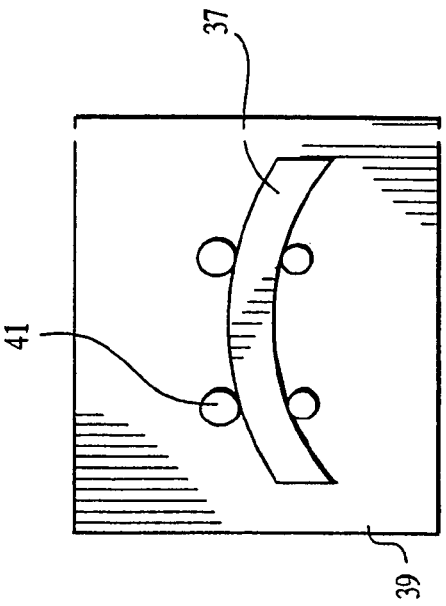
FIG. 12C is a medial view of the recess cutting guide shown in FIG. 12A.
Figure 12A:
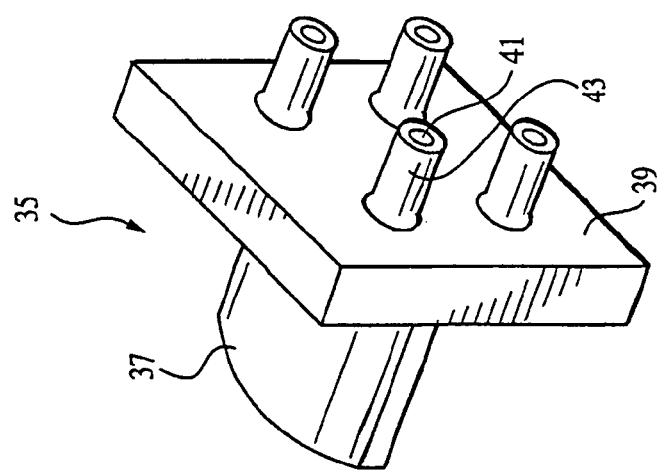
FIG. 12A is a perspective view of a recess cutting guide that is used to make the recesses in the surfaces of the talar dome and the distal tibia.

It can be seen that these prepared surfaces have one or more recesses that run from the lateral to the medial edges of the bones. These recesses are configured so as to match with comparably shaped protrusions and/or shoulders that are parts of the prosthesis' components. The protrusions run from lateral to medial on the prosthesis and allow for greater stability to ankle dorsiflexion and plantarflexion, which occur in a plane perpendicular to the protrusions of the prosthesis. These recesses are positioned and created with the assistance of a recess cutting guide 35. See FIGS. 12A and 12B.

Figure 13A:
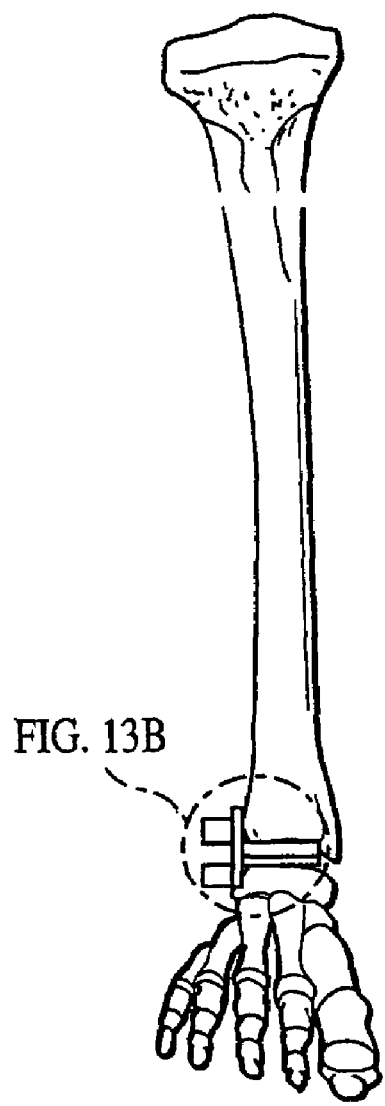
FIG. 13A is an anterior, in-situ view of the recess cutting guide shown in FIG. 12.
Figure 13B:
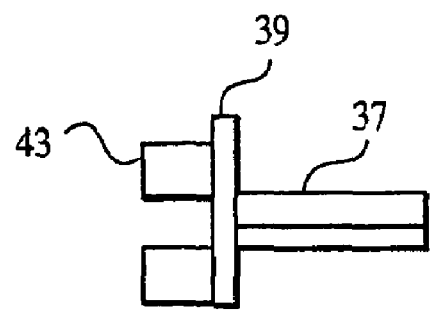
FIG. 13B is a close-up view of the recess cutting guide shown in FIG. 13A.
Figure 14A:
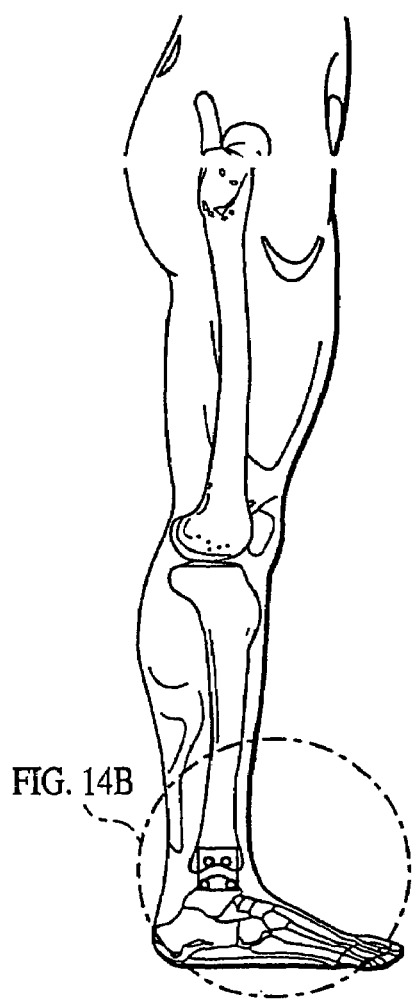
FIG. 14A is a lateral, in-situ view of the recess cutting guide shown in FIG. 12.
Figure 14B:
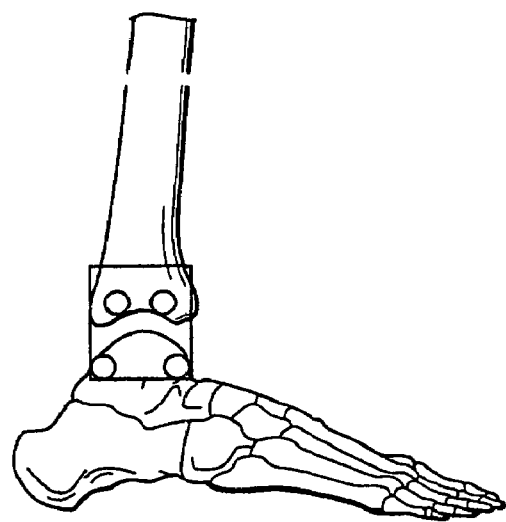
FIG. 14B is a close-up view of the recess cutting guide shown in FIG. 14A.

This recess cutting guide 35 has a curved shelf 37 that is attached to a vertical clement 39 that runs both superiorly and inferiorly. In the vertical element are several holes 41 that have alignment tubes 43 extending from them. These holes and their alignment tubes extend parallel to the surface of curved shelf 37. The curved shelf 37 narrow so that it can be positioned between the distracted tibia and talus. See FIGS. 13A and 13B. With the curved shelf 37 held firmly opposed to the superior surface the talus, it is pinned to the talus with narrow wires through the alignment tubes positioned near the anterior and posterior aspects of the guide. A narrow wire is passed down the curved shelf 37 for each recess and the orientation and location of each narrow wire is inspected on anterior-to-posterior and lateral x-ray views of the ankle. Once the location of the recesses is determined, one or more stabilization recesses are created in the talus with a tapered drill, which tapers from lateral to medial. See FIGS. 14A and 14B.

The ankle joint prosthesis of the present invention can take the form of either a two or a three component embodiment, which may be referred to below as either the mobile bearing or the semi-constrained versions, respectively. These are separately described below.

Figure 15A:
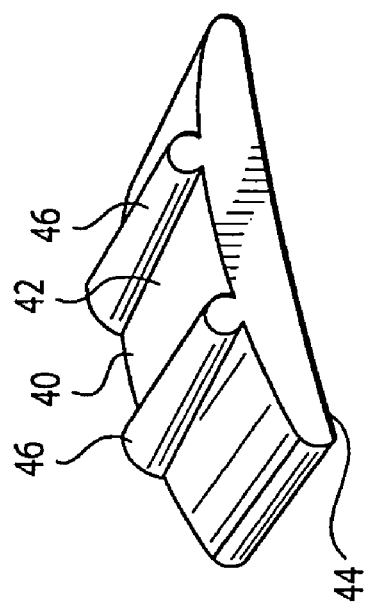
FIG. 15A is a perspective, medial side view of the tibial component of FIG. 15 in which the component's top surface protrusions are tapered.
Figure 15:
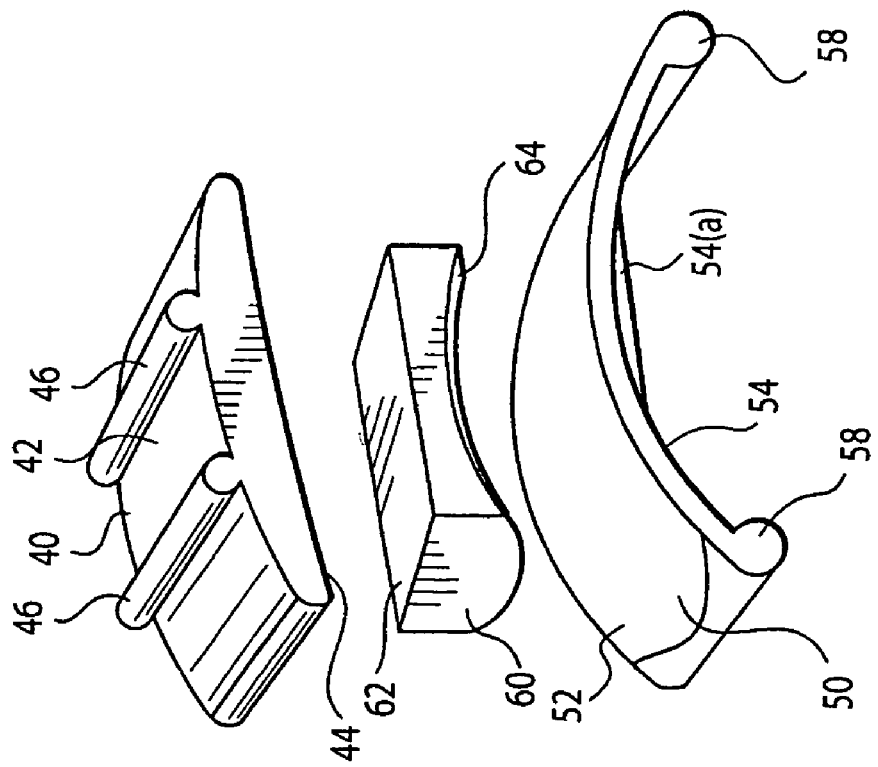
FIG. 15 is a perspective, medial side view of a preferred, mobile bearing embodiment of the ankle joint prosthesis of the present invention.
Figure 16:
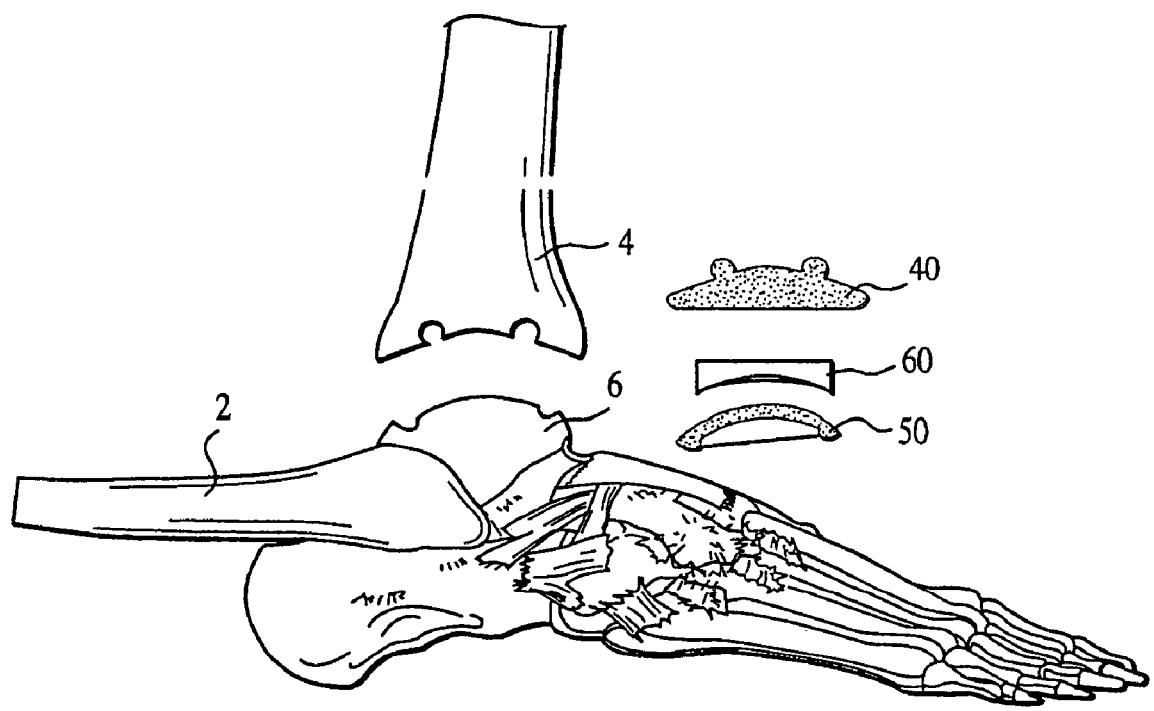
FIG. 16 is a similar view of the foot in FIG. 1 and showing the mobile bearing, ankle joint prosthesis that is to be inserted in place of the removed portions of the distal tibia and talar dome.

FIG. 15 is a perspective, side view of a preferred, mobile bearing embodiment of the ankle joint prosthesis of the present invention. It consists of tibial 40, talar 50 and mobile bearing 60 components, where the tibial 40 and talar 50 components are mounted respectively on the prepared, crescentic-shaped tibial and talar surfaces. The mobile bearing component 60 is located between the tibial 40 and talar 50 components. See also FIG. 16.

The tibial component 40 has a top surface 42 that has convex curvature in the anterior to posterior direction so as to approximate the curvature of the prepared distal tibia surface. Its bottom surface 44 is flat. The top surface 42 has one or more lateral-to-medially aligned protruding surfaces 46 that are configured to match with the similarly shaped recesses that have been made in the tibia's prepared surface. These protrusions 46 serve to stabilize any motion of the component 40 relative to the prepared distal tibia surface and provide greater surface area for bony ingrowth or cement fixation of the component to the tibia. These protrusions may be tapered, from narrow medial to wide lateral, so as to create a more secure and stable fit as the device is inserted from lateral to medial. The component's top surface 42 may be coated with a substance to enhance bony ingrowth or cement fixation. This material may be sintered beads, plasma sprayed, implex/trabecular metal (implex) or other material that provides an interlocking mechanism.

The talar component 50 is a crescentic-shaped structure that is curved on both its top 52 and bottom 54 surfaces. Its the top surface 52 has convex curvature in the anterior to posterior direction and concave curvature in its lateral to medial direction. Its bottom surface 54 has concave curvature in the anterior to posterior direction that approximates the natural curvature found on the prepared talus dome. At some point the talar component's bottom surface, preferably at its anterior and posterior edges, are protrusions or ridges 58 that extend downward from its bottom surface 54. The shape of these protrusions 58 is configured to match with the similarly shaped recesses or extrusions that have been made in the talar dome's prepared surface. These protrusions 58 serve to stabilize any motion of this component 50 relative to the prepared talar dome surface and provide greater surface area for bony ingrowth or cement fixation of the component 50 to the talar dome.

The component's bottom surface 54 may be coated with a substance to enhance bony ingrowth or cement fixation. The medial side of talar component 50 has a shoulder 54(a) extending downward from the top surface that coincides with the prepared medial surface of the talus.

The talar component of the prosthesis effectively serves to semi-resurface the medial and lateral oblique joint surfaces (the "gutters") of the ankle. It does this by resurfacing the medial facet on the tibial side and the lateral facet on the talar side. Both the tibial and the talar portions of the superior articulating surface are fully resurfaced.

The mobile bearing component 60 has a flat top surface 62 and a saddle-shaped bottom surface 64. The bottom surface 64 is configured with a saddle-shaped configuration so as to match with the talar component's top surface 52 and to allow for internal and external rotation motions. This saddle-shaped surface also allows for dorsiflexion and plantar flexion motion. The mobile bearing's top surface 62 is flat match with the shape of the tibia component's flat, bottom surface 44. This flat surface allows for internal and external rotation motions.

These components 40, 50, 60 may preferably be made of any appropriate material suitable for the surgical environment. High density, ultra-high molecular weight polyethylene is an excellent plastic material for the bearing surfaces. It is widely used in other surgical devices and characterized by excellent wear resistance and a low coefficient of friction. Titanium or cobalt chrome alloys, or ceramics, are materials commonly used for the components that are rigidly attached to the bony surfaces.

The mobile bearing embodiment of ankle joint prosthesis described above can also have various versions. For example, in some application it is preferred to use a talar component 50 having a top surface 52 that has only convex curvature in the anterior to posterior direction. Since the bottom surface 64 of the mobile bearing component 60 must have matching and complimentary curvature, this surface 64 also has only convex curvature in the anterior to posterior direction. See FIGS. 17A-1, 17A-2, 17B-1 and 17B-2 for a comparison of the various types of curvatures that can be used in the mobile bearing component's bottom surface.

Due to talar bony deformities, it may also be useful to have a talar component that does not use the crescentic cut, but a flat cut. For example, the talar dome may be depressed or collapsed and there is not room to perform the crescentic cut. A talar component 70, again with various bearing surface curvatures 71 and 72, may have a flat surface 73 on the inferior or bottom surface. Again a medial to lateral directed protrusion 74 provides great surface area for fixation and additional stability.

Figure 19B:
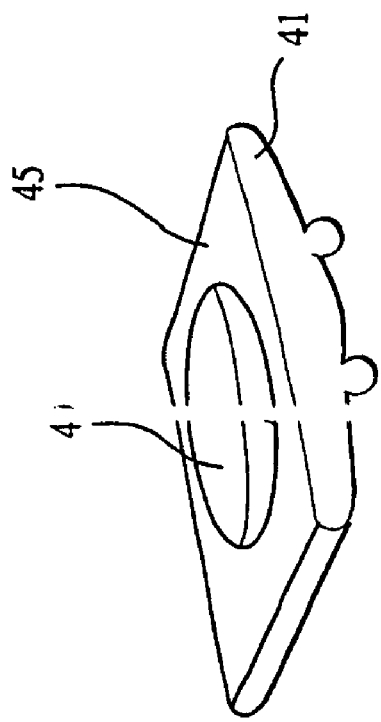
FIG. 19B shows the bottom view of the tibial component shown in FIG. 19A.
Figure 19A:
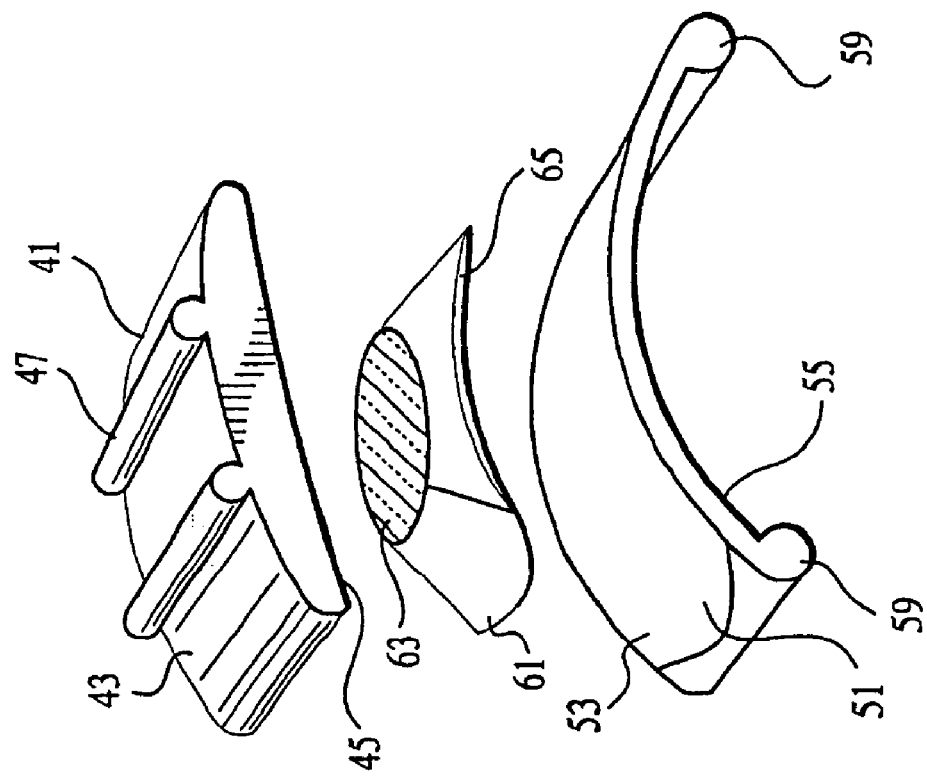
FIG. 19A is a perspective, medial side view of a semi-constrained bearing embodiment in which the bearing component's top surface has a dome that partially locks this component into the matching concavity or recess that exists in the tibial component's bottom surface.

In a preferred, semi-constrained bearing embodiment, the prosthesis consists of a tibial 41, semi-constrained bearing 61 and talar 51 components, where the tibial 41 and talar 51 components are mounted respectively on the prepared, crescentic-shaped tibial and talar surfaces. See FIG. 19A.

In this embodiment, the tibial component 41 has a top surface 43 that has convex curvature in the anterior to posterior direction so as to approximate the curvature of the prepared distal tibia surface. This top surface 43 has one or more lateral-to-medially aligned protruding surfaces 47 that are configured to match with the similarly shaped recesses that have been made in the tibia's prepared surface. These protrusions 47 serve to stabilize any motion of the component 41 relative to the prepared distal tibia surface and provide greater surface area for bony ingrowth or cement fixation of the component to the tibia. These protrusions 47 may be tapered, from narrow medial to wide lateral, so as to create a more secure and stable fit as the device is inserted from lateral to medial. The component's top surface 43 may be coated with a substance to enhance bony ingrowth or cement fixation. This material may be sintered beads, plasma sprayed, implex/trabecular metal (implex) or other material that provides an interlocking mechanism. 3

The tibial component's bottom surface 45 has one of a variety of forms of curvature that are designed to yield various degrees of constraint for the underlying semi-constrained bearing component 61. This bearing component 61 is preferably made from polyethylene or other suitable bearing material, whereas, the tibial and talar components are made from one of a variety of suitable metals. See FIGS. 18A-1, 18A-2, 18B-1 and 18B-2 for a comparison of the various types of curvatures that can be used in the tibial component's bottom surface.

The semi-constrained bearing component's top surface maybe bonded or mechanically attached to the bottom surface of the tibial component 41. The semi-constrained bearing component 61 may also be partially locked into the tibial component 41. For example, its superior aspect 63 may be slightly convex to match a slightly concave curvature that is placed in the bottom surface of the tibial component 41. See FIG. 19A which shows a semi-constrained bearing embodiment in which the bearing component's top surface has a dome that partially locks this component into the matching concavity or recess 49 that exists in the tibial component's bottom surface. See FIG. 19B for the bottom view of the tibial component shown in FIG. 19A. In locked and unlocked versions, the inferior aspect 65 of the semi-constrained bearing component 61 will have different configurations depending on the constraint required.

In this semi-constrained bearing embodiment, the talar component 51 has a top surface 53 with curvature that matches and is complementary to the curvature found in the semi-constrained bearing component's bottom surface 65. The talar component's bottom 55 surface has concave curvature or is approximately flat in the anterior to posterior direction that approximates the natural curvature or flat saw cut found on the prepared talus dome. At some point on the talar component's bottom surface, preferably at its anterior and posterior edges, are protrusions or ridges 59 that extend downward from its bottom surface 57. See FIGS. 20A-1 to 20A-3 and 20B-1 to 20B-3. The shape of these protrusions 59 is configured to match with the similarly shaped recesses or extrusions that have been made in the talar dome's prepared surface. These protrusions 59 serve to stabilize any motion of this component 51 relative to the prepared talar dome surface and provide greater surface area for bony ingrowth of the component 51 to the talar dome. The lateral side of talar component 51 has a shoulder 55(a) extending downward from the top surface that coincides with the prepared lateral surface of the talus. The component's bottom surface 55 may be coated with a substance to enhance bony ingrowth or cement fixation.

In the semi-constrained bearing embodiment, the tibial and talar components may be wider medially than laterally so as to approximated the native truncated cone shape of the talus.

To mount the tibial 40 and talar 50 components in place, the protrusions 46 and/or shoulders 56 of these component are carefully aligned with the matching recesses or groves that have been prepared in the respective distal tibia and talar dome surfaces. The medial edges of these components are abutted against the lateral edges of the grooves. A surgical mallet maybe used to apply light blows to the lateral edges of the components to drive the medial edges of their protrusions and/or shoulders into the matching grooves until the components are fully seated in the respective tibial and talar dome surfaces. These components become adhered to tibial and talar dome cut surfaces by cement fixation or by press fitting and later bony ingrowth.

Figure 21:
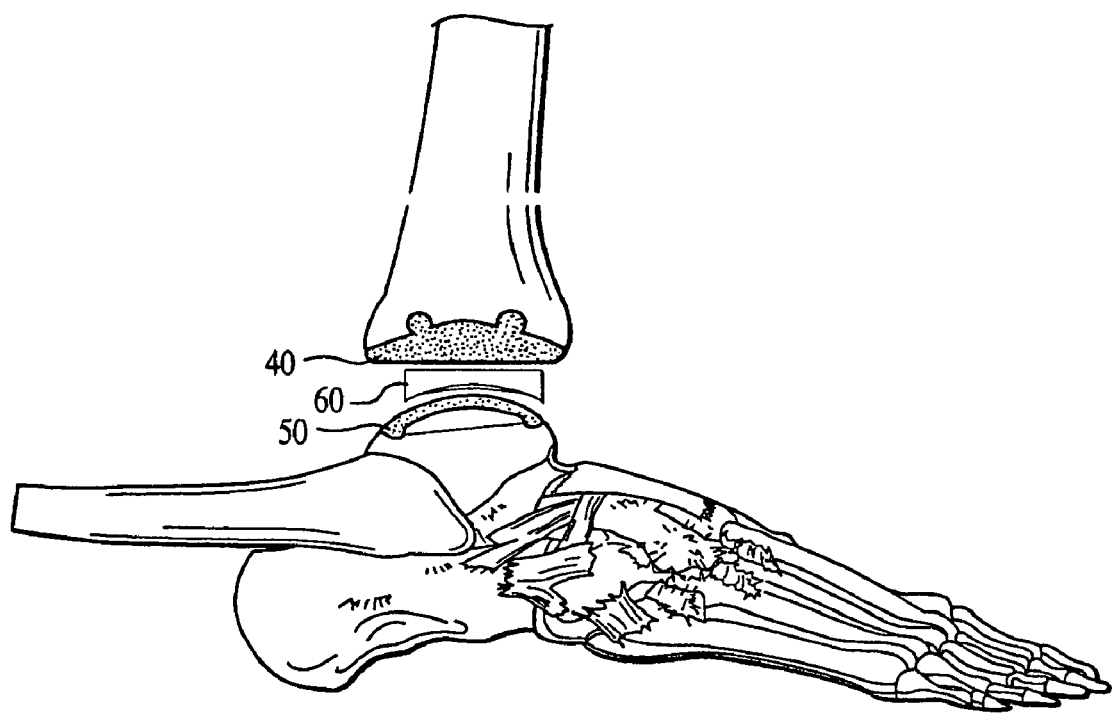
FIG. 21 is a similar view of the foot in FIG. 1 and showing the ankle joint prosthesis components after they have been inserted in place of the removed portions of the distal tibia and talar dome.
Figure 22:
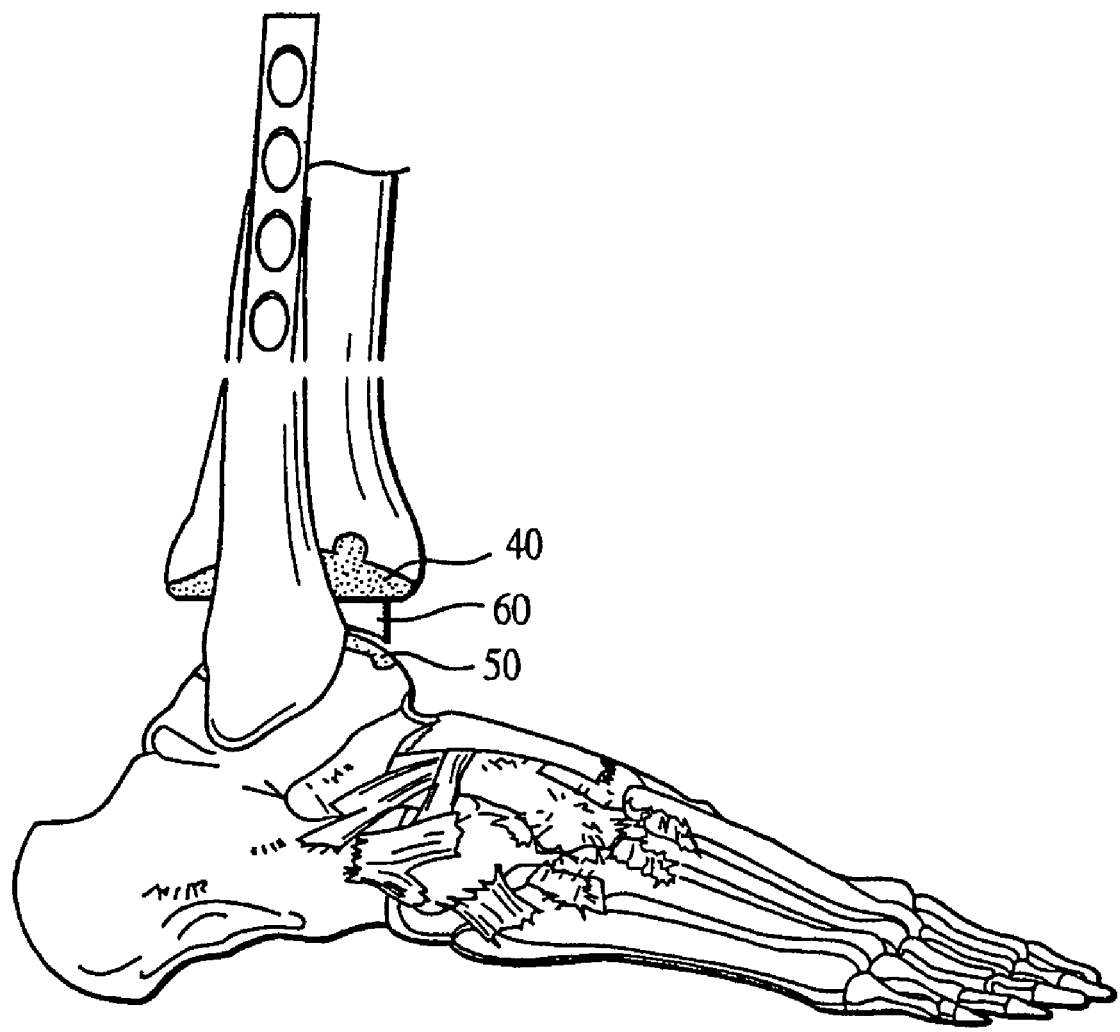
FIG. 22 is a similar view of the foot in FIG. 1 and showing the ankle joint prosthesis components inserted, the ankle distraction removed and the fibula placed back in position and plated in place.

The mobile bearing component 60 may be properly located and seated within the ankle joint, between the tibial component 40 and the talar component 50, by hand. The mobile bearing component is inserted into the ankle joint with the foot in distracted position. FIG. 21 illustrates the completed ankle joint for the mobile bearing embodiment of the prosthesis with all of the prosthesis' components in place. FIG. 22 illustrates the ankle prosthesis components inserted, the ankle distraction removed and the fibula placed back in position and plated in place.

If the completed ankle joint is too lax, a mobile bearing component 60 of greater thickness may be chosen. Similarly, if the completed ankle joint is too tight, a mobile bearing 60 of lesser thickness can be used. Selection of the mobile bearing component 60 of proper thickness permits adjustment of the overall height of the prosthesis.

For the semi-constrained bearing embodiment of the prosthesis, different thickness of the tibial or talar components are used to accomplish the same fitting objectives discussed above.

Although the foregoing disclosure relates to preferred embodiments of the invention, it is understood that these details have been given for the purposes of clarification only. Various changes and modifications of the invention will be apparent, to one having ordinary skill in the art, without departing from the spirit and scope of the invention as hereinafter set forth in the claims.

We claim:

1. An ankle joint prosthesis adapted to involve the patient's distal tibia and talus, said prosthesis comprising:
  a tibial component for lateral to medial implanting on a prepared portion of said distal tibia, said tibial component having a top and a bottom surface, said top surface having convex curvature in the anterior to posterior direction and configured so as to compliment and match with the curvature of said prepared portion of said distal tibia, said bottom surface being approximately flat,
  a talar component for lateral to medial implanting on a prepared portion of said talus, said talar component having a top and a bottom surface and a lateral edge, said top surface having convex curvature in the anterior to posterior direction, said bottom surface having concave curvature in the anterior to posterior direction and configured so as to compliment and match with the curvature of said prepared portion of said talus, and a mobile bearing component for lateral to medial implanting between said tibial and talar components, said bearing component having a top and a bottom surface, said top surface being approximately flat, said bottom surface having concave curvature in the anterior to posterior direction that is complementary to the curvature of said talar component's top surface.

2. The ankle joint prosthesis as recited in claim 1, wherein:

said tibial component top surface having a lateral-to-medially aligned protrusion that is configured to match with a similarly shaped recess that has been made in the prepared portion of said distal tibia.

3. The ankle joint prosthesis as recited in claim 1, wherein:

said talar component bottom surface having a lateral-to-medially aligned protrusion that extends downward from an edge chosen from the group of anterior and posterior edges, said protrusion configured to match with a similarly shaped recess that has been made in the prepared portion of said talus.

4. The ankle joint prosthesis as recited in claim 2, wherein:

said talar component bottom surface having a lateral-to-medially aligned protrusion that extends downward from an edge chosen from the group of anterior and posterior edges, said protrusion configured to match with a similarly shaped recess that has been made in the prepared portion of said talus.

5. The ankle joint prosthesis as recited in claim 1, wherein:

said talar component having an anterior-to-posterior aligned shoulder that extends downward from the lateral edge of said talar component top surface.

6. The ankle joint prosthesis as recited in claim 2, wherein:

said talar component having an anterior-to-posterior aligned shoulder that extends downward from the lateral edge of said talar component top surface.

7. The ankle joint prosthesis as recited in claim 3, wherein:

said talar component having an anterior-to-posterior aligned shoulder that extends downward from the lateral edge of said talar component top surface.

8. The ankle joint prosthesis as recited in claim 4, wherein:

said talar component having an anterior-to-posterior aligned shoulder that extends downward from the lateral edge of said talar component top surface.

9. The ankle joint prosthesis as recited in claim 1, wherein:

said talar component top surface having concave curvature in the lateral to medial direction, and said mobile bearing component bottom surface having convex curvature in the lateral to medial direction that is complementary to the curvature of said talar component's top surface in the lateral to medial direction.

10. The ankle joint prosthesis as recited in claim 2, wherein:

said talar component top surface having concave curvature in the lateral to medial direction, and said mobile bearing component bottom surface having convex curvature in the lateral to medial direction that is complementary to the curvature of said talar component's top surface in the lateral to medial direction.

11. The ankle joint prosthesis as recited in claim 3, wherein:

said talar component top surface having concave curvature in the lateral to medial direction, and said mobile bearing component bottom surface having convex curvature in the lateral to medial direction that is complementary to the curvature of said talar component's top surface in the lateral to medial direction.

12. The ankle joint prosthesis as recited in claim 4, wherein:

said talar component top surface having concave curvature in the lateral to medial direction, and said mobile bearing component bottom surface having convex curvature in the lateral to medial direction that is complementary to the curvature of said talar component's top surface in the lateral to medial direction.

13. The ankle joint prosthesis as recited in claim 5, wherein:

said talar component top surface having concave curvature in the lateral to medial direction, and said mobile bearing component bottom surface having convex curvature in the lateral to medial direction that is complementary to the curvature of said talar component's top surface in the lateral to medial direction.

14. The ankle joint prosthesis as recited in claim 2, wherein:

said tibial protrusion being tapered, from narrow medial to wide lateral, so as to create a more secure and stable fit for said tibial component.

15. The ankle joint prosthesis as recited in claim 4, wherein:

said tibial protrusion being tapered, from narrow medial to wide lateral, so as to create a more secure and stable fit for said tibial component.

16. The ankle joint prosthesis as recited in claim 8, wherein:

said tibial protrusion being tapered, from narrow medial to wide lateral, so as to create a more secure and stable fit for said tibial component.

17. The ankle joint prosthesis as recited in claim 1, wherein:

said tibial component top surface being coated with a substance to enhance adhesion between said component and prepared, distal tibia surface.

18. The ankle joint prosthesis as recited in claim 1, wherein:

said talar component bottom surface being coated with a substance to enhance adhesion between said component and prepared, talar surface.

19. The ankle joint prosthesis as recited in claim 17, wherein:

said coating substance being chosen from the group consisting of sintered beads, plasma sprayed, implex/trabecular metal or other material that provides an interlocking mechanism for better adhesion between said tibial component and prepared, distal tibia surface.

20. The ankle joint prosthesis as recited in claim 18, wherein:

said coating substance being chosen from the group consisting of sintered beads, plasma sprayed, implex/trabecular metal or other material that provides an interlocking mechanism for better adhesion between said talar component and prepared, talar surface.

21. The ankle joint prosthesis as recited in claim 1, wherein:

said components being fabricated from materials chosen from the group consisting of an ultra-high, molecular weight polyethylene, titanium or cobalt chrome alloys.

* * * * *